United States Patent
Rzigalinski et al.

(10) Patent No.: US 10,857,178 B2
(45) Date of Patent: Dec. 8, 2020

(54) CERIUM OXIDE NANOPARTICLES FOR TREATMENT AND PREVENTION OF ALZHEIMER'S DISEASE, PARKINSON'S DISEASE, AND DISORDERS ASSOCIATED WITH FREE RADICAL PRODUCTION AND/OR MITOCHONDRIAL DYSFUNCTION

(75) Inventors: Beverly A. Rzigalinski, Radford, VA (US); Neeraj Singh, Blacksburg, VA (US); Courtney A. Cohen, Frederick, MD (US)

(73) Assignee: EDWARD VIA VIRGINIA COLLEGE OF OSTEOPATHIC MEDICINE, Blacksburg, VA (US)

( * ) Notice: Subject to any disclaimer, the term of this patent is extended or adjusted under 35 U.S.C. 154(b) by 924 days.

(21) Appl. No.: 12/252,905

(22) Filed: Oct. 16, 2008

(65) Prior Publication Data
US 2009/0092671 A1 Apr. 9, 2009

Related U.S. Application Data

(63) Continuation-in-part of application No. 11/993,260, filed as application No. PCT/US2006/024963 on Jun. 27, 2006, now abandoned.

(60) Provisional application No. 60/980,345, filed on Oct. 16, 2007, provisional application No. 60/980,354, filed on Oct. 16, 2007, provisional application No. 60/693,930, filed on Jun. 27, 2005.

(51) Int. Cl.
| | |
|---|---|
| A61K 33/24 | (2019.01) |
| A61K 9/14 | (2006.01) |
| A61P 5/28 | (2006.01) |
| A61P 25/28 | (2006.01) |

(52) U.S. Cl.
CPC .............. *A61K 33/24* (2013.01); *A61K 9/14* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 7,347,987 B2 * | 3/2008 | McGinnis et al. ............... | 424/59 |
| 7,534,453 B1 * | 5/2009 | Rzigalinski et al. .......... | 424/617 |
| 2003/0231992 A1 | 12/2003 | Sarkas et al. | |
| 2006/0246152 A1 | 11/2006 | McGinnis et al. | |
| 2010/0166821 A1 * | 7/2010 | Rzigalinski et al. ......... | 424/423 |

OTHER PUBLICATIONS

Chinopoulos et al., Mitochondria deficient in complex I activity are depolarized by hydrogen peroxide in nerve terminals: relevance to Parkinson's disease, Journal of Neurochemistry (2001), vol. 76, pp. 302-306.*
Dacey, Dopamine-Accumulating Retinal Neurons Revealed by in Vitro fluorescence Display a Unique Morphology, Science (1988), vol. 240, pp. 1196-1198.*
STN online, file CAPLUS, Acc. No. 1999:461445, Doc. No. 131:155866 (Wang et al., Protective effect of cerium on mitochondria wheat under salinity stress, Zongguo Xitu Xuebao (1999), vol. 17, No. 2, pp. 187-190), Abstract.*
Smeyne et al., PNAS (2007), vol. 104, No. 6, pp. 1997-1982.*
Patil, Electronic Theses and Disertation (2006), Paper 1094, pp. 1-111.*
Mazibuko et al., Journal of Pharmaceutical Sciences (2015), vol. 104, pp. 1213-1229.*
Singh et al., Ann. N. Y. Acad. Sci. (2007), vol. 1122, pp. 219-230.*
Rzigalinski et al., Experimental Biology (2003): Meeting Abstracts, 377.24, p. A606.*
U.S. Appl. No. 11/993,260, filed Jun. 27, 2006.
Rzigalinski, B.A. et al., "Cerium oxide nanoparticles increase the lifespan of cultured brain cells and protect against free radical and mechanical trauma", (Abstract #377.24, 2003 Experimental Biology meeting abstracts (online).
PCT Search Report and Written Opinion; PCT/US2006/024963.
European Extended Search Report; European patent application 06785640.1-2123.
Cook et al., "Neuronal damage induced by polychlorinated biphenyls is partially reversed by cerium oxide nanoparticles", Annual Meeting of the Society of Neuroscience, XX, XX, vol. 2003, Jan. 1, 2003, Abstract No. 669.13.
Callaghan P.G. et al., "Deleterious effects of microglia activated by in vitro trauma are blocked by engineered oxide nanoparticles," Society for Neuroscience Abstract Viewer and Itinerary Planner, vol. 2003, 2003, Abstract No. 11.7, 33$^{rd}$ Annual Meeting of the Society of Neuroscience, New Orleans, LA, Nov. 8-12, 2003.
Fry, R. et al. "Engineered oxide nanoparticles protect against neuronal damage associated with in vitro trauma", Society for Neuroscience Abstract Viewer and Itinerary Planner, vol. 2003, 2003, Abstract No. 552.9, 33$^{rd}$ Annual Meeting of the Society of Neuroscience, New Orleans, LA, Nov. 8-12, 2003.

(Continued)

*Primary Examiner* — Monica A Shin
(74) *Attorney, Agent, or Firm* — Tarolli, Sundheim, Covell & Tummino LLP

(57) ABSTRACT

Cerium oxide nanoparticles (CeONP) can be used to treat or prevent neurodegenerative diseases, including for example Alzheimer's Disease, Parkinson's Disease, Huntington's Disease, AIDS-related dementia, ALS, progressive supranuclear palsy, and encephalitis, as well as mitochondrial diseases and diseases associated with mitochondrial damage. In particular, CeONP having an average size of about 2 nm to about 100 nm can be administered in an amount sufficient to block production of hydroxyl or superoxide radicals, block free radical production by $A\beta_{(1-42)}$, block $A\beta_{(1-42)}$-induced neuronal death, block $A\beta_{(1-42)}$-induced $[Ca^{2+}]_i$ dysfunction in neurons, block $A\beta_{(1-42)}$-induced lipid peroxidation, decrease loss of dopaminergic neurotransmission, or reduce mitochondrial dysfunction in a cell. CeONP can also be effective in treating conditions involving toxic exposures to compounds that induce mitochondrial dysfunction, such as rotenone, cyanide, carbon monoxide, polychlorinated biphenyls (PCBs) and other mitochondrial toxins.

6 Claims, 15 Drawing Sheets

(56) References Cited

OTHER PUBLICATIONS

Clark A. et al., "Engineered oxide nanoparticles increase neuronal lifespan in culture and act as free radical scavengers", Society for Neuroscience Abstract Viewer and Itinerary Planner, vol. 2003, 2003, Abstract No. 878.2, 33rd Annual Meeting of the Society of Neuroscience, New Orleans, LA, Nov. 8-12, 2003.

Strawn E.T. et al.., "Cerium oxide nanoparticles increase lifespan and protect against free radical medicated toxicity", FASEB Journal, vol. 20, No. 5, Part 2, Mar. 2006, p. A1356.

Schubert D. et al., "Cerium and yttrium oxide nanoparticles are neuroprotective", Biochemical and Biophysical Research Communications, vol. 342, No. 1, Mar. 31, 2006, pp. 86-91.

Rzigalinski, B.A., "Nanoparticles and cell longevity", Technology in Cancer Research & Treatment, vol. 4, No. 6, Dec. 2005, pp. 651-659.

Szilagyi G. eta al., "Visualization of mitochondrial membrane potential and reactive oxygen species via double staining", Neuroscience Letters, Limerick, IE, vol. 399, No. 3, May 22, 2006, pp. 206-209.

* cited by examiner

Cerium Oxide Nanoparticles (CeONP) Scavenge Hydroxyl Radicals

Cerium Oxide Nanoparticles Scavenge Superoxide Radicals

Cerium Oxide Nanoparticles Block Aβ$_{(1-42)}$-Induced Free Radical Formation

Cerium Oxide Nanoparticles Decrease Aβ$_{(1-42)}$-Induced Neuronal Death

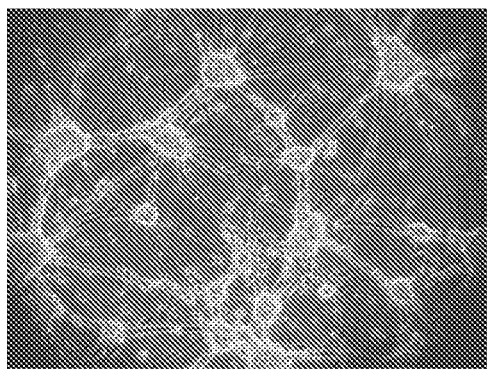
Figure 5A – Light Micrograph, Healthy, Pure Cortical Neuronal Cultures - Magnification 100x
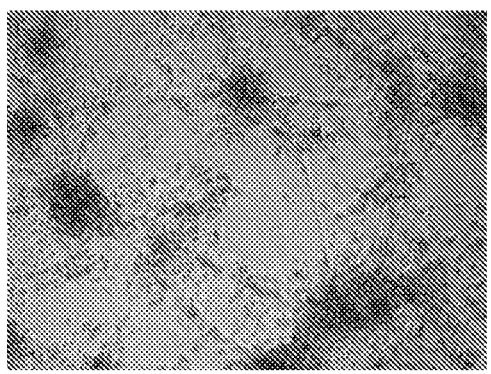
Figure 5B – Light Micrograph, Pure Cortical Neuronal Cultures, Treated with 10 μM $A\beta_{(1-42)}$ - Magnification 100x
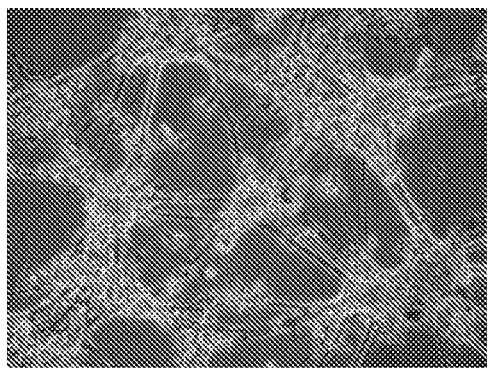
Figure 5C – Light Micrograph, Pure Cortical Neuronal Cultures, Treated with 10 nM Cerium Oxide Nanoparticles and Exposed to $A\beta_{(1-42)}$ - Magnification 100x Cerium Oxide Nanoparticles Reduce Aβ-Induced Elevation of Basal Intracellular Free Calcium in Neurons Cerium Oxide Nanoparticles Protect Neurons from $A\beta_{(1-42)}$-Induced Alterations in Glutamate-Mediated Calcium Signaling Cerium Oxide Nanoparticles Inhibit A$\beta_{(1-42)}$-Induced Lipid Peroxidation Cerium Oxide Nanoparticles Extend Lifespan of Female Drosophila after Exposure to High Dose (10 mM) Paraquat Cerium Oxide Nanoparticles Extend Lifespan of Male Drosophila after Exposure to High Dose (10 mM) Paraquat Cerium Oxide Nanopartiles Protect Female Drosophila from Low Dose (1mM) Paraquat and Extend Post-Paraquat Lifespan Cerium Oxide Nanoparticles Protect Male Drosophila from Low Dose (1mM) Paraquat and Extend Post-Paraquat Lifespan Cerium Oxide Nanoparticles Preserve Motor Function in Paraquat-Challenged Female Drosophila Cerium Oxide Nanoparticles Preserve Motor Function in Paraquat-Challenged Male Drosophila

Cerium Oxide Nanoparticles Preserve Climbing to 8 cm in Paraquat-Challenged Female Drosophila

Cerium Oxide Nanoparticles Preserve Climbing to 8 cm in Paraquat-Challenged Male Drosophila

CeONP Localized in Mitochondria of Mixed Organotypic Neuronal Cultures

Cerium Oxide Nanoparticles Protect Mixed Organotypic Brain Cell Cultures from Cell Injury Induced by Rotenone Cerium Oxide Nanoparticles Preserve Mitochondrial Membrane Potential after Rotenone Challenge

CERIUM OXIDE NANOPARTICLES FOR TREATMENT AND PREVENTION OF ALZHEIMER'S DISEASE, PARKINSON'S DISEASE, AND DISORDERS ASSOCIATED WITH FREE RADICAL PRODUCTION AND/OR MITOCHONDRIAL DYSFUNCTION

CROSS-REFERENCE TO RELATED APPLICATIONS

This application relies on the disclosure and claims the benefit of the filing date of U.S. Provisional Application Nos. 60/980,345 and 60/980,354, both filed Oct. 16, 2007, and this application is a continuation-in-part application of U.S. patent application Ser. No. 11/993,260, filed Dec. 20, 2007 now abandoned, published as U.S. Patent Application Publication 2010/0166821, which is a U.S. national stage application of PCT/US2006/024963, filed Jun. 27, 2006, which claims priority to U.S. Provisional Application No. 60/693,930, filed Jun. 27, 2005, the disclosures of all of which are incorporated herein by reference in their entireties.

STATEMENT OF GOVERNMENT INTEREST

This invention was made partially with U.S. Government support from the United States National Institutes of Health under contract No. AG022617 (National Institute on Aging). The U.S. Government has certain rights in the invention.

BACKGROUND OF THE INVENTION

Field of the Invention

The present invention relates to the field of medicine and treatment of medically relevant diseases, disorders, and complications of aging. More specifically, the invention relates to the use of nanoparticles to treat subjects suffering from various diseases, disorders, and complications due to aging.

Description of Related Art

Alzheimer's and Parkinson's diseases, neuromuscular disorders, and mitochondrial diseases are associated with increased oxidative stress, production of free radicals, and/or destruction of mitochondria. It has previously been shown that cerium oxide nanoparticles (CeONP) decrease oxidative stress, reduce free radical production, and extend cell and organism longevity. See, e.g., International Patent Application Publication No. WO 2007/002662; Rzigalinski, B. A., K. Meehan, R. M. Davis, Y. Xu, W. C. Miles, and C. A. Cohen, Radical Nanomedicine, Nanomedicine 1, 399-412, 2006 ("Rzigalinski I (2006)"); Rzigalinski, B., I. Danelisen, E. Strawn, C. Cohen, and C. Liang, Biological Nanoparticles for Cell Engineering—A Radical Concept, in Nanotechnologies for Life Sciences, C. Kumar, Editor, Wiley & Sons, 2006 ("Rzigalinski II (2006)"); Rzigalinski, B., Nanoparticles and cell longevity, Tech. Cancer Res. Treatment, 4, 651-660, 2005 ("Rzigalinski 2005"); and Singh, N., C. A. Cohen, and B. A. Rzigalinski, Treatment of Neurodegenerative disorders with radical nanomedicine, Ann. N.Y. Acad. Sci., 1122, 222-230, 2007 ("Rzigalinski 2007"). Here, it is further demonstrated that CeONP has utility as a potential treatment and preventative strategy for these disorders.

Alzheimer's Disease (AD) is a devastating illness currently affecting 25 million people worldwide and is the 5th leading cause of death in the United States. See, e.g., Evans, D A, H H Funkenstein, M S Albert, P A Scherr, N R Cook, M J Chown, L E Herbert, C H Hennekens, & J O Taylor, Prevalence of Alzheimer's Disease in a community population of older persons—Higher than previously reported, JAMA 262, 2551-2556, 1989. AD is primarily a disease of an aging population and with a rapidly increasing aging population, the burden of AD will reach even broader proportions in the near future.

Presently, pharmacotherapy for AD is limited to treatment of cholinergic and glutamatergic deficits and aimed at maintaining existing cognitive function and hopefully slowing the decline in neuronal function and neuronal death associated with AD. To date, however, treatment is only minimally effective at best. See, e.g., Swaab, D F, E J G Dubelaar, E J A Scherder, E J W van Someren, and R W H Verwer, Therapeutic strategies for Alzheimer Disease, Alz. Dis. Assoc. Disord., 17, S114-S112, 2003.

AD is associated with 2 basic diagnostic pathologies, deposition of amyloid beta (Aβ) protein in plaques and development of neurofibrillary tangles composed of tau protein. Whether these pathological markers are causative of the disease is a subject of much debate. Several groups hypothesize that development of AD occurs from biochemical insults initiating years upstream of overt development of Aβ plaques, neurofibrillary tangles, and cognitive deficits. Suspect early events are believed to involve increased free radical damage and oxidative stress. Numerous researchers hypothesize that early oxidative stress resulting from low levels of toxic forms of Aβ, $A\beta_{(1-42)}$, may be one of the initiating events which propagates to the full blown disease as we know it. $A\beta_{(1-42)}$ is a product of cellular enzymatic cleavage, and is believed to be the specific form of Aβ associated with AD.

Further, $A\beta_{(1-42)}$ has been shown to generate free radicals and induce free radical-mediated damage to cellular macromolecules. See, e.g., Butterfield, D A, M Perluigi, & R Sultana, Oxidative stress in Alzheimer's Disease brain: new insights from redox proteomics, Eur. J. Pharmacol, 545, 39-50, 2006; Ansari, M A, G Joshi, Q Huang, W O Opii, H M Abdul, R Sultana, & D A Butterfield, In vivo administration of D609 leads to protection of subsequently isolated gerbil brain mitochondria subjected to in vitro oxidative stress induced by amyloid beta-peptide and other oxidative stressors: relevance to Alzheimer's disease and other oxidative-stress related neurodegenerative disorders, Free Rad. Biol. Med., 41, 1694-1703, 2006; Butterfield, D A, T Reed, S F Newman, & R Sultana, Roles of amyloid beta peptide-associated oxidative stress and brain protein modification in the pathogenesis of Alzheimer's disease and mild cognitive impairment, Free Rad. Bio. Med., 43, 658-677, 2007.

Although several hypotheses for development of AD exist, most agree that toxic $A\beta_{(1-42)}$ and oxidative stress are part of the initiating and propagating events of this disease. Prior work with CeONP (see, e.g., WO 2007/002662; Rzigalinski I (2006); Rzigalinski II (2006); Rzigalinski 2005; and Singh 2007) suggests that the radical scavenging antioxidant and neuroprotective activities of CeONP may aid in the treatment and prevention of AD.

Parkinson's Disease (PD) is a devastating neurodegenerative disorder that presently affects 1% of Americans over the age of 50. However several reports indicate that the actual incidence is much higher, due to unrecognized early symptoms (Young R. American Family Physician, Apr. 15, 1999, world-wide-web at aafp.org/afp/990415ap/2155.html.

The disease is characterized by muscle rigidity, tremor, bradykinesia progressing to akinesia, and is caused by progressive loss of dopaminergic neurons in the substantia nigra. PD is primarily a disease of an aging population and with a rapidly increasing aging population, the burden of PD will reach even broader proportions in the near future. Presently, pharmacotherapy for PD is limited to treatment with levodopa or synthetic dopamine agonists, in the hope of stimulating remaining dopaminergic neurons. However to date, there are no effective therapies for slowing the progression of this disease and protecting remaining dopaminergic neurons. Current treatment is only minimally effective at best. Pahwa R. Understanding Parkinson's disease: an update on current diagnostic and treatment strategies, J. Am. Med. Dir. Assoc., 7, 4-10, 2006.

PD is associated with two basic diagnostic pathologies, loss of neurons in the substantia nigra resulting in movement disorders and appearance of intracellular Lewy bodies, containing aggregated forms of the protein α-synuclein. Although several forms of early onset PD are reported to be genetic (Reynolds A, C Lauri, R Lee Mosely, & HE Gendelman, Oxidative stress and the pathogenesis of neurodegenerative disorders, Int. Rev. Neurobiol., 82, 297-325, 2007) most cases of PD are of idiopathic origin.

Several groups hypothesize that development of PD occurs from biochemical insults initiating years upstream of overt development of PD symptomology, similar to AD. See, e.g., Jenner P., Oxidative stress in Parkinson's Disease, Ann. Neurol., 53, S26-S38, 2003; and Hunot S & EC Hirsch, Neuroinflammatory processes in Parkinson's disease, Ann. Neurol., 53, S49-S60, 2003. Suspect early events are believed to involve increased free radical damage and oxidative stress, possibly from exposure to certain toxins such as pesticides. See, e.g., Ascherio A, H Chen, M Weisskopf, Pesticide exposure and risk for Parkinson's disease, Ann. Neurol., 60, 197-203, 2006. Increased oxidative stress appears to be a common denominator for dopaminergic neuronal loss in this disease.

Both AD, PD, and other disease have a common link in mitochondrial dysfunction. Butterfield (2006); Ansari (2006); Reynolds (2007); and Jenner (2003). Mitochondrial dysfunction increases free radical production, and adversely affects cellular energy status. However, the true cause at the molecular level is not known. The present invention relates to examination of the use of CeONP to protect mitochondria directly.

SUMMARY OF THE INVENTION

The present inventors have shown that cerium oxide nanoparticles (CeONP) can be used to treat or prevent neurodegenerative diseases, including for example Alzheimer's Disease, Parkinson's Disease, Huntington's Disease, AIDS-related dementia, ALS, progressive supranuclear palsy, and encephalitis, as well as mitochondrial diseases and diseases associated with mitochondrial damage. For example, the methods, compositions, and particles according to the invention include CeONP having an average size of about 2 nm to about 100 nm that can be administered in an amount sufficient to block production of hydroxyl or superoxide radicals, block free radical production by $A\beta_{(1-42)}$, block $A\beta_{(1-42)}$-induced neuronal death, block $A\beta_{(1-42)}$-induced $[Ca^{2+}]_i$ dysfunction in neurons, block $A\beta_{(1-42)}$-induced lipid peroxidation, decrease loss of dopaminergic neurotransmission, or reduce mitochondrial dysfunction in a cell. CeONP can also be effective in preventing or treating conditions resulting from toxic exposure to compounds that induce mitochondrial dysfunction, including for example rotenone, cyanide, carbon monoxide, polychlorinated biphenyls (PCBs) and other mitochondrial toxins. The invention encompasses use of cerium oxide nanoparticles as described herein for treating or preventing neurodegenerative diseases or an underlying cause of neurodegenerative disease in cells, such as the causes described herein. Use of cerium oxide particles to make a pharmaceutical composition for treating or preventing neurodegenerative diseases or an underlying cause of neurodegenerative disease is also included.

The present invention includes methods of treating or preventing a neurodegenerative disease comprising administering cerium oxide nanoparticles having an average particle diameter size of about 2 nm to about 100 nm in an amount sufficient to block production of hydroxyl or superoxide radicals, block free radical production by $A\beta_{(1-42)}$, block $A\beta_{(1-42)}$-induced neuronal death, block $A\beta_{(1-42)}$-induced $[Ca^{2+}]_i$ dysfunction in neurons, or block $A\beta_{(1-42)}$-induced lipid peroxidation in a cell.

Methods of the invention include treating or preventing neurodegenerative diseases characterized by oxidative stress and free radical production.

The present invention further includes methods for preventing or treating Alzheimer's Disease, Parkinson's Disease, Huntington's Disease, AIDS-related dementia, ALS, progressive supranuclear palsy, or encephalitis.

Methods according to the invention include any method described herein, including in vivo, in vitro, and ex vivo methods of treating or preventing neurodegenerative diseases by administering cerium oxide nanoparticles having an average particle diameter size ranging from about 2 nm to about 100 nm, from about 20 nm to about 50 nm, or about 10 nm to about 20 nm.

Methods of the invention further include methods of treating or preventing a neurodegenerative disease comprising administering cerium oxide nanoparticles having an average particle diameter size of about 2 nm to about 100 nm in an amount sufficient to decrease loss of dopaminergic neurotransmission, to deter or prevent dopaminergic neuronal loss, or to protect dopaminergic neurons in a cell.

The methods according to the invention, in particular as just described, can also be used to treat or prevent Parkinson's Disease and/or restore, increase, or prevent to the decrease of motor function of a subject.

Methods of treating or preventing mitochondrial diseases or effects of mitochondrial toxins are also included in the invention, which comprise administering cerium oxide nanoparticles having an average particle diameter size of about 2 nm to about 100 nm in an amount sufficient to reduce mitochondrial dysfunction in a cell.

Treating or preventing effects of mitochondrial toxins resulting from exposure of a cell to rotenone, cyanide, carbon monoxide, or polychlorinated biphenyls (PCBs) are also included within the scope of the inventive methods.

Mitochondrial dysfunction, including mitochondrial failure resulting from inhibition of mitochondrial Complex I, can be treated or prevented by using methods of the invention described herein.

The present invention further includes methods of treating or preventing mitochondrial dysfunction, wherein the mitochondrial dysfunction is caused by a decrease in mitochondrial membrane potential (MMP) and wherein the amount of cerium oxide nanoparticles is sufficient to increase MMP, deter or prevent a decrease in MMP, or preserve MMP in a cell.

BRIEF DESCRIPTION OF THE DRAWINGS

FIGS. 5A, 5B, and 5C show light micrographs of cortical neuronal cultures, untreated, treated with 10 μM $A\beta_{(1-42)}$, and treated with 10 nM cerium oxide nanoparticles (average size 10-20 nm) and exposed to $A\beta_{(1-42)}$.

DETAILED DESCRIPTION OF VARIOUS EMBODIMENTS OF THE INVENTION

Figure 1:
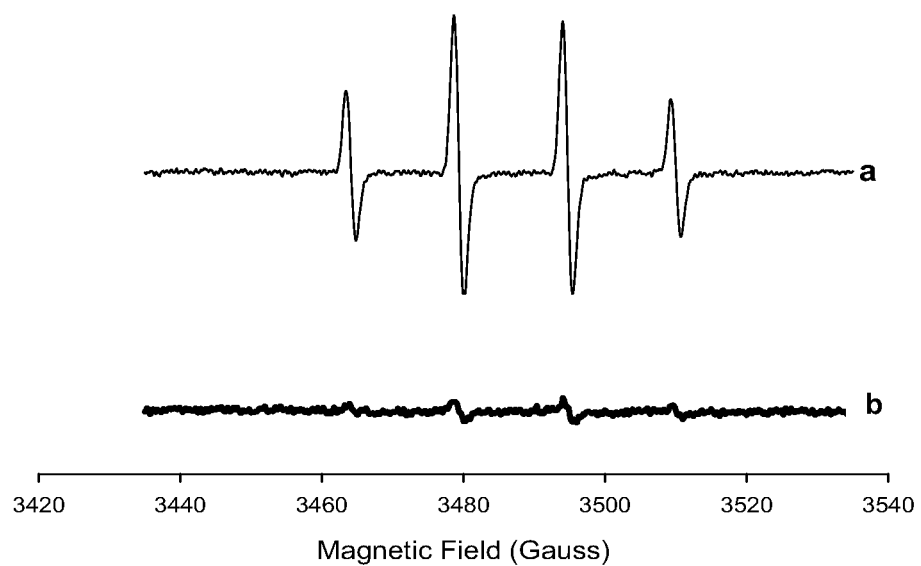
FIG. 1 shows an EPR tracing showing the effect of the presence of cerium oxide nanoparticles on quenching hydroxyl radical production.

Reference will now be made in detail to various exemplary embodiments of the invention. The following detailed description is presented for the purpose of describing certain embodiments in detail. Thus, the following detailed description is not to be considered as limiting the invention to the embodiments described. Rather, the true scope of the invention is defined by the claims.

In the examples that follow, the inventors used cerium oxide nanoparticles available from Nanophase Technologies Corporation (Romeoville, Ill.). Synthesis of these particles has been described in the following patents: U.S. Pat. Nos. 6,669,823, 5,460,701, 5,514,349, 5,874,684; Japanese Patents JP2980987 and JP3383608; European Patent EP0711217B1; German Patent DE69426886; French Patent FR94922757; Great Britain Patent GB94922757; and Australian Patent AU068582882, the disclosures of which are hereby incorporated by reference in their entirety. Advantages of using these CeONP are further described in the inventors' prior work, e.g., WO 2007/002662, the disclosure of which is hereby incorporated by reference in its entirety.

The inventors have found that CeONP having an average particle size ranging from about 2 nm to about 100 nm in diameter may be used for preventing or treating neurodegenerative diseases, mitochondrial diseases, and effects of mitochondrial toxins. The inventors have found, more particularly, that CeONP ranging from about 2 nm to about 50 nm are preferable. CeONP ranging from about 10 nm to about 20 nm may be even more preferable. Of course, depending on the application, any specific size or size range within these general sizes can be provided, the size being selected by the practitioner based on situation-specific parameters.

The present invention provides methods of treating individuals suffering from, or suspected of suffering from neurodegenerative diseases, as well as methods of preventing such diseases. The invention also provides methods of treating or preventing injury resulting or caused by exposure to toxic substances. The methods include in vitro, in vivo, and/or ex vivo methods of treating or preventing neurodegenerative diseases. Administering CeONP according to the invention can comprise any act that provides cerium oxide nanoparticles to a subject (e.g., individual, animal, patient, etc.) in a way that the particles can function for their intended purpose. In general, a dosing of about 0.01 ng to about 1 g, such as about 0.05 ng, 0.1 ng, 0.5 ng, 1 ng, 10 ng, 50 ng, 100 ng, 500 ng, 1 ug, 5 ug, 10 ug, 50 ug, 100 ug, 500 ug, or 1 g per administration or per kg body mass per administration should be effective in providing the desired therapeutic or prophylactic result. Of course, depending on the application and according to the practitioner's specifications, any dose in this range may be used to prevent or treat neurodegenerative diseases.

I. Alzheimer's Disease.

1.1. Cerium Oxide Nanoparticles block hydroxyl radical production in vitro. To demonstrate that CeONP directly inhibit free radical formation, we used electron paramagnetic resonance spectroscopy (EPR) to measure the ROS scavenging activity of CeONP. Hydroxyl radicals were generated by adding 250 μl of 0.2 M $H_2O_2$ to a solution containing 0.025M DMPO (spin trap) and 1.7 mM $FeSO_4$ in 0.17M potassium phosphate buffer, pH 7.4. Radical production was detected with a Bruker ER 200D ESR spectrometer, at 37° C.

In the tracings shown in FIG. 1, the number of radicals produced is proportional to the intensity of the peaks shown in the EPR signal. Control experiments demonstrated that CeONP alone (in the presence of DMPO) did not induce hydroxyl radical formation (data not shown). Hydroxyl radicals generated via the Fenton reaction are shown in trace (a). In trace (b), 0.5 mg CeONP (average size about 10-20 nm) was added. As shown, hydroxyl radical production was almost completely quenched. CeONP with average sizes from about 2 nm to 50 nm produced similar quenching of hydroxyl radicals, with an average size of about 10-20 nm being the most effective in vitro size.

Figure 2:
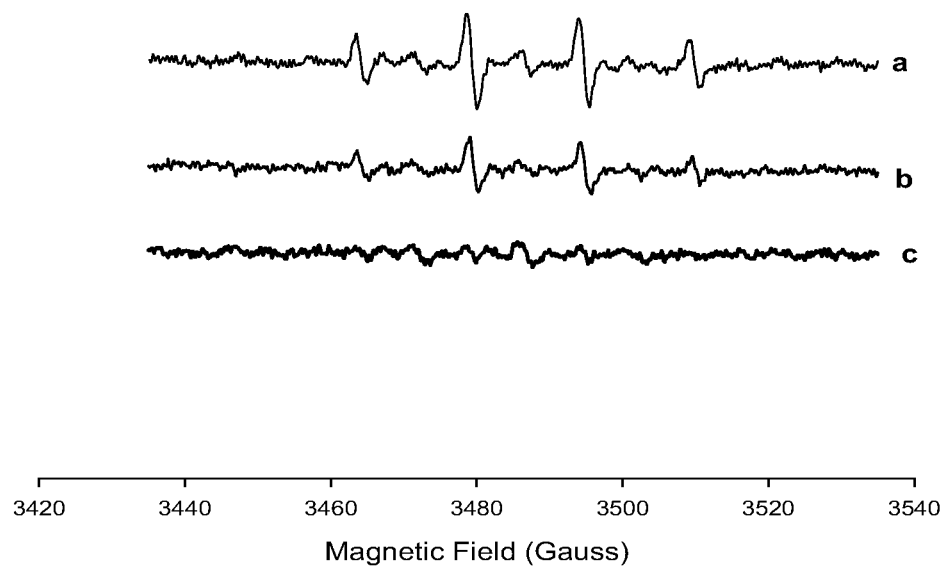
FIG. 2 shows an EPR tracing showing the effect of the presence of cerium oxide nanoparticles on quenching superoxide radical production.

1.2. Cerium oxide nanoparticles block superoxide radical production in vitro. The ability of CeONP to block superoxide radical production in vitro was also examined, as is shown in FIG. 2. Superoxide radicals were generated by irradiating a solution of riboflavin (0.53 mM) and DMPO (0.1 M) in potassium phosphate buffer (0.17M) pH 7.4, with a UV lamp for 10 min. Trace (a) shows the superoxide generated by EPR measurement of the spectrum of the DMPO/O2-adduct. In trace (b), 0.5 mg of 7 nm ceria NP was added, which reduced superoxide production. In trace (c), 0.5 mg of 10-20 nm (average size) CeONP was added, showing almost complete quenching of superoxide production. Similar quenching of superoxide production was observed with 50 nm average size CeONP (data not shown).

CeONP alone produced no superoxide radicals. Taken together, these EPR results demonstrate directly that CeONP, preferably having a size range of about 2-50 nm, reduce superoxide radical production in vitro.

1.3. Cerium oxide nanoparticles block free radical production by $A\beta_{(1-42)}$. It has been shown that the toxic or disease producing fragment of $A\beta$, $A\gamma_{(1-42)}$, produces free radicals (Butterfield (2007); Kanski, J, S Varadarajan, M Aksenova, & D A Butterfield, Role of glycine-33 and methionine-35 in Alzhemier's amyloid β-peptide 1-42-associated oxidative stress and neurotoxicity, Biochim. Biophys. Acta., 1586, 190-198, 2001; and Varadarajan, S, J Kanski, M Aksenova, C. Lauderbeck, and D. A. Butterfield, Different mechanisms of oxidative stress and neurotoxicity for Alzheimers Aβ (1-42) and Ab(25-35), J. Am. Chem. Soc., 123, 5625-5631, 2001), which are suspected to be an initiating event in the development of AD. We reproduced the generation of free radicals by $A\beta_{(1-42)}$ as described by the Butterfield group (Butterfield (2007); Kanski (2001); and Varadarajan (2001), the disclosures of which are incorporated by reference herein in their entirety).

Figure 3:
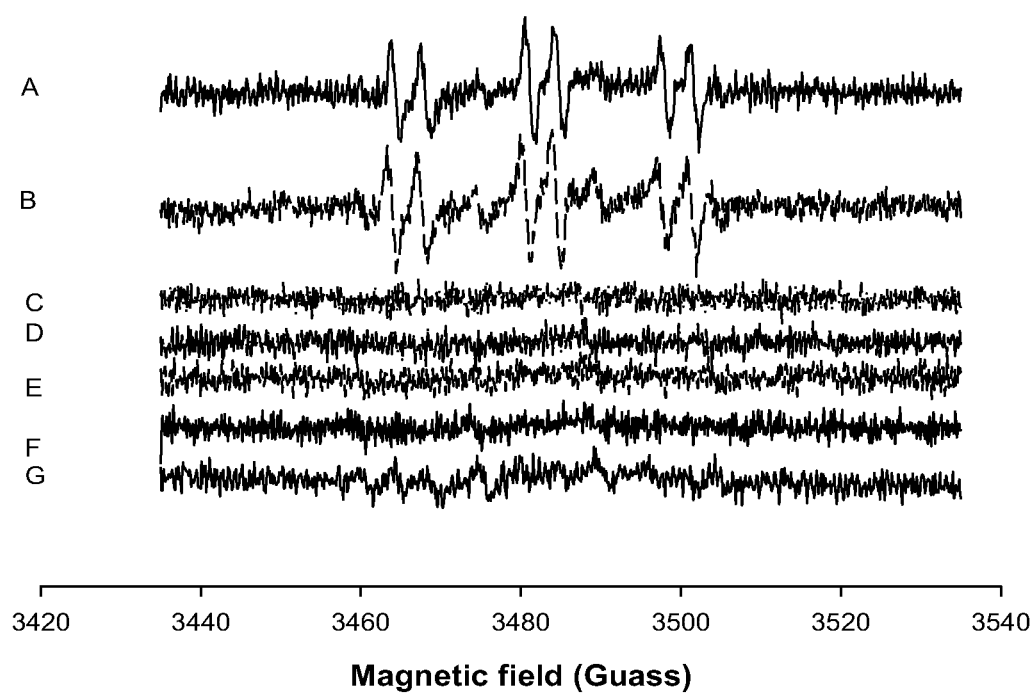
FIG. 3 shows an EPR tracing showing that cerium oxide nanoparticles block $A\beta_{(1-42)}$-induced free radical formation.

$A\beta_{1-42}$ (1 mg/ml) was incubated at 37° C. in chelexed phosphate buffered saline containing PBN as a spin trap, in an EPR flat cell. Incubation periods were varied from 4-16 days. Cohen, C. A., et al. (2006), CeO2 Nanoparticles Extend Lifespan and Protect Drosophila Melanogaster from Paraquat-Induced Oxidative Stress, Free. Rad. Biol. & Med., 123, the disclosure of which is incorporated by reference herein in its entirety. Flat cells were examined by EPR at 12-24 hr intervals, for production of free radicals. As shown in FIG. 3 (trace A), $A\beta_{1-42}$ produced a characteristic "fingerprint" free radical spectra beginning on day 4 and persisting through day 16 (trace B). Incubation of $A\beta_{142}$ with CeONP (0.5 mg) completely blocked free radical production induced by $A\beta_{1-42}$ (FIG. 3, trace C). To ascertain whether cerium simply delayed free radical production, flat cells containing $A\beta_{1-42}$ or cerium+$A\beta_{1-42}$ were monitored via EPR for up to 16 days (data not shown). Free radicals continued to be produced by $A\beta_{1-42}$ solutions, but were completely blocked at all time points by addition of cerium oxide (data not shown). Cerium oxide alone (trace E) or cerium plus albumin (trace D) showed no free radical production, demonstrating that nonspecific protein incubation does not generate free radicals. Traces F and G represent controls of CeONP alone and CeONP with spin trap, demonstrating no radical production. Taken together, these results suggest that CeONP block free radical production associated with $A\beta_{1-42}$ in vitro.

1.4. Cerium oxide nanoparticles reduce $A\beta_{(1-42)}$ toxicity in pure neuronal cultures. It is well known that $A\beta_{1-42}$ is toxic to neurons in culture. Pure neuronal cultures were prepared from the cortices of embryonic rats using established procedures (Weber, J. T., Rzigalinski, B. A., Willoughby, K. A., Moore, S. F., & Ellis, E. F. (1999), Alterations in calcium-mediated signal transduction and intracellular calcium stores after in vitro injury of pure embryonic neurons, Cell Calcium, 26, 289-299, the disclosure of which is incorporated herein by reference in its entirety) and treated with CeONP (10 nM, 10-20 nanometer average size) or vehicle (normal saline) on day 6 in vitro, for 48 hrs.

Prior studies (see, e.g., WO 2007/002662; Rzigalinski I (2006); Rzigalinski II (2006); Rzigalinski 2005; and Singh 2007, the disclosures of which are incorporated by reference herein in their entirety) demonstrate that CeONP are taken up by the cells during this time period. Molar references (i.e., 10 nM CeONP) correlate to a CeONP suspension containing 10 nM of cerium, since the exact molecular weight of a single CeONP is unknown.

Figure 4:
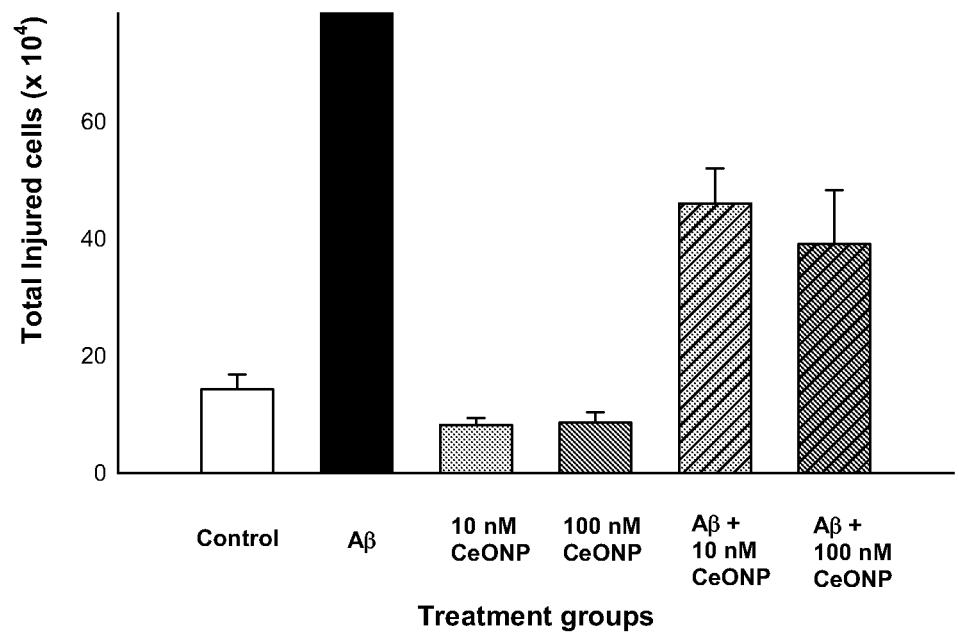
FIG. 4 is a bar graph that shows cerium oxide nanoparticles decrease $A\beta_{(1-42)}$-induced neuronal death.

CeONP solutions for delivery were prepared by 2 min probe sonication of concentrated stocks and all serial dilutions. On day 10 in vitro, neurons were exposed to vehicle (saline) or $A\beta_{1-42}$ (10 μM) and cell death was assessed by propidium iodide staining 48 hrs later. Propidium iodide is normally excluded from uninjured cells, but enters cells with damaged or disrupted membranes, staining the nucleus a brilliant orange. As shown in FIG. 4, CeONP inhibited $A\beta_{1-42}$-induced cell death 42-53%, depending on the dose. FIGS. 5A, 5B, and 5C show light micrographs of pure neuronal cultures treated with saline or CeONP, followed by challenge with 10 μM $A\beta_{(1-42)}$. FIG. 5A shows healthy 12 day old neuronal cultures. Note distinct cells bodies and tightly cabled axonal processes. FIG. 5B shows neurons treated with $A\beta_{(1-42)}$ on day 10 in vitro. Note the disintegrating cell bodies and fragmented axons. FIG. 5C shows neurons treated with CeONP, followed by $A\beta_{(1-42)}$, demonstrating preservation of healthy, normal, neurons.

1.5. Cerium oxide nanoparticles block $A\beta_{(1-42)}$-induced calcium dysregulation in neurons. Intracellular free calcium ($[Ca^{2+}]_i$) is an important signaling process in neurons and other cells. In unstimulated cells, $[Ca^{2+}]_i$ is generally maintained at a low level (50-100 nM). During a signaling event such as muscle contraction or neurotransmission in the brain, $[Ca^{2+}]_i$ is elevated as a signal is propagated. In order to effectively transmit and propagate signaling information, $[Ca^{2+}]_i$ must be maintained at a normal basal level. As neurons and other cells are injured and go on to die, failure of ionic gradients such as $[Ca^{2+}]_i$ occur, and basal $[Ca^{2+}]_i$ becomes elevated, often prior to cell death.

We measured $[Ca^{2+}]_i$ in neurons exposed to 10 μM $A\beta_{(1-42)}$ with and without CeONP treatment. $[Ca^{2+}]_i$ was measured with Fura-2 microspectrophotometry, as previously described. (See, e.g., Weber (1999); Zhang, L., B. A. Rzigalinski, E. F. Ellis, & L. S. Satin (1997), Reduction of voltage-dependent Mg2+ blockade of NMDA currents in mechanically injured cortical neurons, Science 274, 1805-1976; Rzigalinski, B. A., Willoughby, K. A., Hoffman, S., Falck, J. R., & Ellis, E. F. (1999) Calcium influx factor: Further evidence it is 5,6-epoxyeicosatrienoic acid, J. Biol. Chem., 274, 175-182; and Ahmed, S. M., Weber, J. T., Rzigalinski, B. A., & Ellis, E. F. (2002), NMDA receptor contributes to a portion of the decreased mitochondrial membrane potential and elevated intracellular free calcium in strain-injured neurons, J. Neurotrauma, 19, 1619-29, the disclosures of which are incorporated by reference herein in their entirety.)

Figure 6:
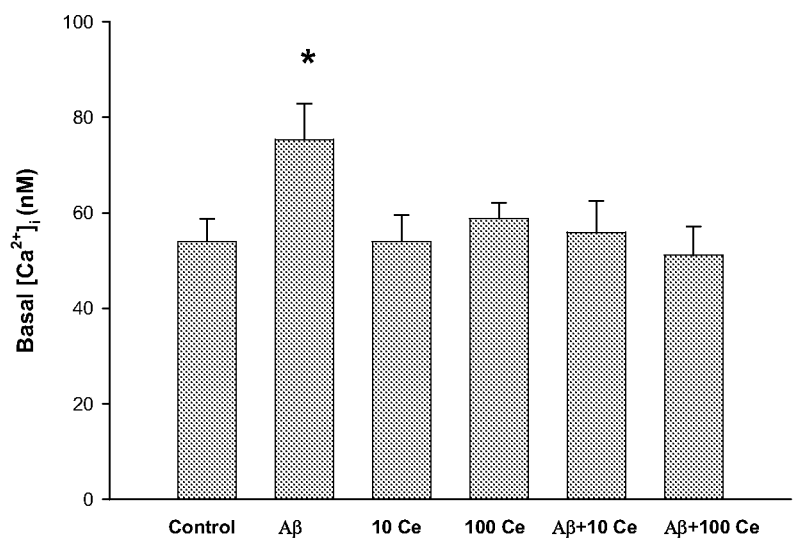
FIG. 6 is a bar graph that demonstrates that cerium oxide nanoparticles reduce Aβ-induced elevation of basal intracellular free calcium in neurons.

As shown in FIG. 6, pure cultures of rat embryonic cortical neurons were treated with CeONP (avg size 10-20 nm) on day 6 in vitro. For the control, neurons were treated with saline. On day 10, cultures were treated with 10 μM $A\beta_{(1-42)}$. Results are derived from fields of 10-15 neurons in 3 separate experiments. Intracellular free calcium ($[Ca^{2+}]_i$) was measured with Fura-2 microspectrophotometry on days 12-13. As shown, control and CeONP-treated neurons had similar basal $[Ca^{2+}]_i$ levels, while $A\beta_{(1-42)}$ significantly increased basal (unstimulated) $[Ca^{2+}]_i$ in neurons, which was reduced to normal levels by pretreatment with 10 and 100 nM cerium oxide nanoparticles (i.e. pretreatment with CeONP protected against the $A\beta_{(1-42)}$-induced elevation in basal $[Ca^{2+}]_i$).

In addition to basal $[Ca^{2+}]_i$ levels, neurons also undergo an elevation in $[Ca^{2+}]_i$ during a neurotransmission event. A primary excitatory neurotransmitter in the brain is glutamate. In AD, both cholinergic and glutamatergic signaling decline as the disease progresses. Therefore, we examined the effect of CeONP on neuronal glutamate signaling after $A\beta_{(1-42)}$ challenge. Neurons were treated with CeONP followed by $A\beta_{(1-42)}$ challenge as described in 1.4 above.

Figure 7:
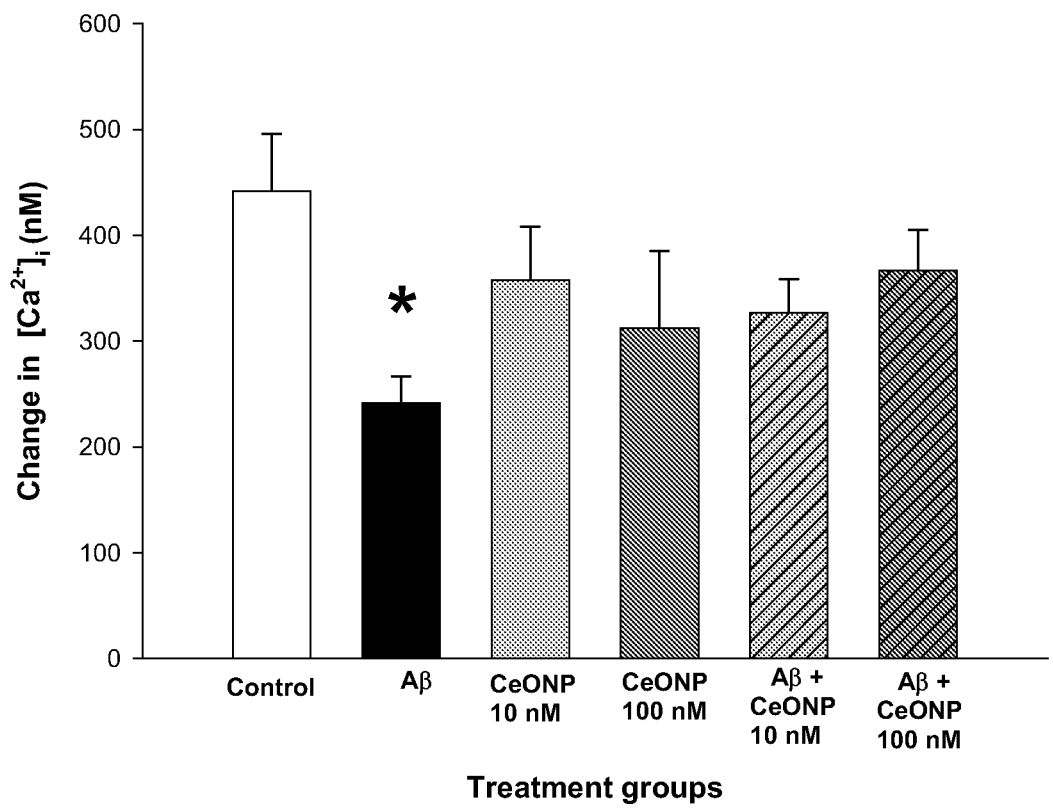
FIG. 7 is a bar graph that shows that cerium oxide nanoparticles protect neurons from $A\beta_{(1-42)}$-induced alterations in glutamate-mediated calcium signaling.

Glutamate-stimulated $[Ca^{2+}]_i$ signaling was assessed as previously described (see, e.g., Weber (1999); Zhang (1997); Rzigalinski (1999); and Ahmed (2002), the disclosures of which are incorporated by reference herein in their entirety). Results shown are derived from populations of 10-15 neurons from 3 separate experiments. FIG. 7 shows the average glutamate-stimulated change in $[Ca^{2+}]_i$ produced by 100 μM glutamate, 427±71 nM in controls. Pure cultures of rat embryonic cortical neurons were treated with cerium oxide nanoparticles (avg size 10-20 nm) on day 6 in vitro. On day 10, cultures were treated with 10 μM $A\beta_{(1-42)}$. Intracellular free calcium was measured with Fura-2 microspectrophotometery as described in FIG. 6. Glutamate (100 μM) was used as a stimulus and the change in $[Ca^{2+}]_i$ was measured. As shown, $A\beta_{(1-42)}$ decreased the glutamate-stimulated change in $[Ca^{2+}]_i$, which was blocked by CeONP. In particular, CeONP treated neurons had similar levels of glutamate-stimulated $[Ca^{2+}]_i$ elevation (bars 3 and 4). Neurons treated with $A\beta_{(1-42)}$ showed a significantly decreased response to glutamate, 230±42 ($2^{nd}$ bar), demonstrating that $A\beta_{(1-42)}$ decreases glutamate signaling in neurons. In CeONP-treated neurons, $A\beta_{(1-42)}$ had no effect on glutamate signaling, which was maintained within the normal range (bars 5 and 6).

Taken together, these data demonstrate that CeONP effectively prevent the $A\beta_{(1-42)}$-induced dysfunction in $[Ca^{2+}]_i$ signaling and protect neurons from the deleterious effects of $A\beta_{(1-42)}$.

1.6. Cerium oxide nanoparticles decrease $A\beta_{(1-42)}$-induced lipid peroxidation in neurons. AD and $A\beta_{(1-42)}$ are also associated with formation of free radical damage products to cellular macromolecules, particularly lipids. (Markesbery, W. R. & Lovell, M. A., Damage to lipids, proteins, DNA, and RNA in mild cognitive impairment, Arch. Neurol., 64, 954-966, 2007.)

Figure 8:
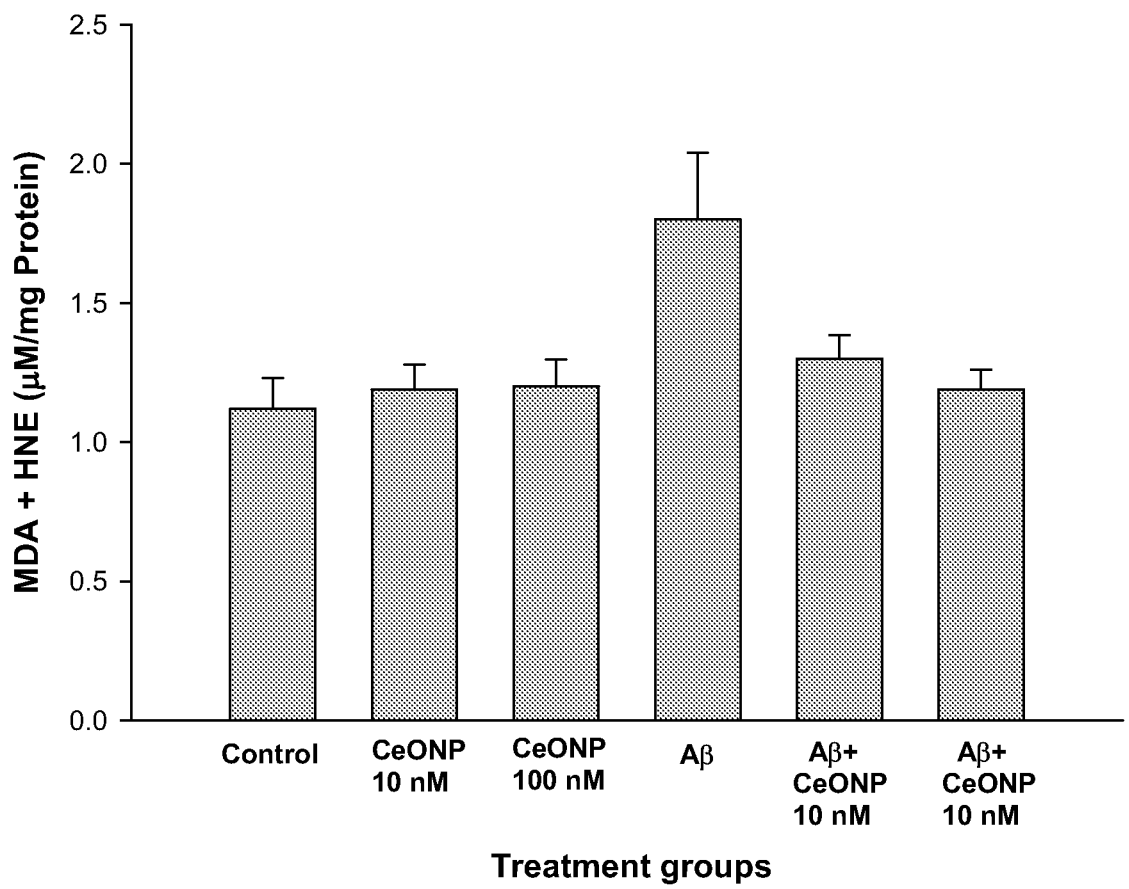
FIG. 8 is a bar graph that shows that cerium oxide nanoparticles inhibit $A\beta_{(1-42)}$-induced lipid peroxidation.

We assessed the effect of CeONP on $A\beta_{(1-42)}$-induced lipid damage by measuring lipid peroxidation products in $A\beta_{(1-42)}$-treated neuronal cultures, as shown in FIG. 8. Pure cultures of rat embryonic cortical neurons were treated with cerium oxide nanoparticles (avg size 10-20 nm) on day 6 in vitro. On day 10, cultures were treated with 10 μM $A\beta_{(1-42)}$. Two days after $A\beta_{(1-42)}$ treatment, lipid peroxidation products (LPO) were measured with a spectrophotometric kit from Invitrogen, and represent the sum total of malondialdehyde (MDA) and hydroxynonenal (HNE), both of which are toxic lipid peroxidation products. Lipid peroxidation products were normalized to the amount of protein in each cell culture well, using a modified Lowry protein assay. As shown in FIG. 8, $A\beta_{(1-42)}$ treatment increased lipid peroxidation, which was inhibited by CeONP treatment. In particular, the levels of LPO in controls treated with saline or CeONP alone (as described in section 1.4) are shown in the first three bars of FIG. 8. There was no significant difference in LPO in CeONP vs. saline treated neurons on day 12 in vitro. $A\beta_{(1-42)}$ treatment dramatically increased LPO in controls as shown. The $A\beta_{(1-42)}$-induced increase in LPO was blocked by CeONP administration, as shown in the last 2 bars of FIG. 8. These results demonstrate that CeONP block $A\beta_{(1-42)}$-induced lipid peroxidation in neurons.

II. Parkinson's Disease.

Here, we demonstrate the utility of CeONP in treatment of Parkinson's Disease using a Drosophila model of Parkinson's disease, exposure to the herbicide toxin paraquat. See, e.g., Meulener M, Whitworth A J, Armstrong-Gold C E, Rizzu P, Heutink P, Wes P D, Pallanck L G, Bonini N M, Drosophila DJ-1 mutants are selectively sensitive to environmental toxins associated with Parkinson's disease, Curr. Biol., 15, 1572-1577, 2005; and Cicchetti F, Lapointe N, Roberge-Tremblay A, Saint-Pierre M, Jimenez L, Ficke B W, Gross R E, Systemic exposure to paraquat and maneb models early Parkinson;s disease in young adult rats, Neurobiol. Dis., 20, 360-371, 2005, the disclosures of which are incorporated by reference herein in their entirety. FIGS. 9A-B, 10A-B, 11A-B, and 12A-B show the results.

In Drosophila, paraquat induces a dose dependent motor dysfunction and death, in part, by destruction of dopaminergic neurons through superoxide generation. For these studies, male and female Drosophila of the Oregon R strain were cultured as previously described. Rzigalinski I (2006); and Cohen (2006), the disclosures of which are incorporated by reference herein in their entirety.

Experiments were conducted on cohorts of 100 male or female flies. One hundred newly enclosed male or female flies were placed in control or CeONP treated food (10 nM-100 μM, 10 flies per vial) for days 1-30 of their lifespan. Fly food consisted of Jazz Mix with CeONP added in suspensions containing 1 μM docusate sodium for even dispersion of nanoparticles in the food mix. On day 30, flies were placed in empty vials for 1 hr, followed by transfer to vials containing filter paper saturated with 5% sucrose containing 1 or 10 mM paraquat, for 1 hr. After paraquat exposure, flies were returned to their respective food groups. Death counts were performed at intervals thereafter. Results shown represent 2-3 separate experiments on cohorts of 100 flies.

2.1. Cerium oxide nanoparticles protect Drosophila from paraquat. CeONP protected against paraquat toxicity, decreasing mortality and increasing lifespan in treated flies. CeONP protected against paraquat toxicity in male flies, at a higher dose than that utilized in females.

Figure 9A:
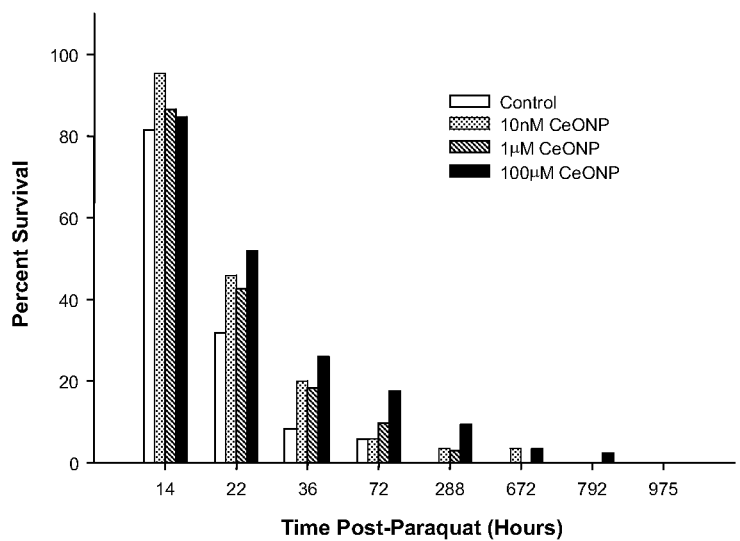
FIGS. 9A and 9B are bar graphs that show that cerium oxide nanoparticles extend the lifespan of male and female Drosophila after exposure to high dose (10 mM) paraquat.
Figure 9B:
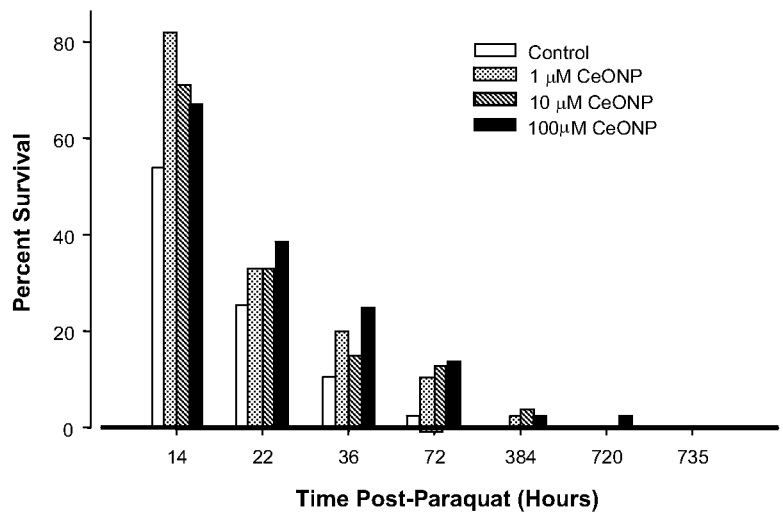

In particular, as shown in FIG. 9A, exposure to 10 mM paraquat resulted in rapid death of untreated female flies, with over 75% death by 22 hrs post-paraquat. However females treated with 10 nM-100 μM CeONP showed enhanced survival and outlived their untreated age matched controls. Similar results were observed in male Drosophila (FIG. 9B). However the dose required for paraquat resistance in males was higher (1 μM-100 μM) than that required for females.

Figure 10A:
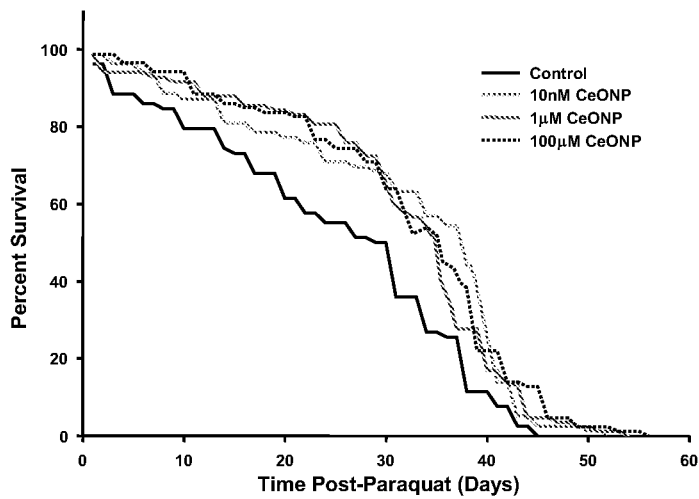
FIGS. 10A and 10B are line graphs that show that cerium oxide nanoparticles protect female and male Drosophila from low dose (1 mM) paraquat and extend post-paraquat lifespan.
Figure 10B:
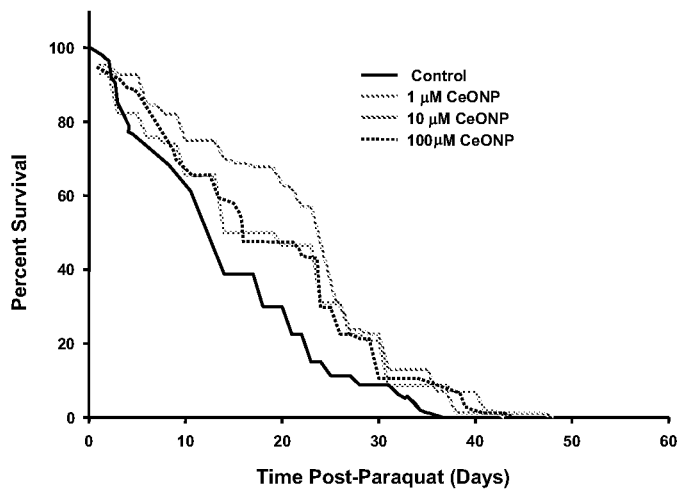

A paraquat dose of 10 mM is a high, lethal dose for flies at age 30 (mid-life). Therefore, we also examined a lower dose of paraquat, 1 mM, as shown in FIGS. 10A and 10B. One hundred female and one hundred male Drosophila were treated with CeONP delivered in the fly food, as described above. The mortality curve for female flies exposed to 1 mM paraquat on day 30 is shown in FIG. 10A, black solid line. Flies died steadily after paraquat exposure (time zero on the graph) with all flies in the cohort of 100 dying by 44 days post-paraquat. CeONP treated flies showed increased survival post-paraquat, with CeONP treated groups surviving 52-56 days post-paraquat. Similar results were observed in male flies exposed to 1 mM paraquat on day 30, as shown in FIG. 10B. Taken together, these results demonstrate that CeONP increase survival and decrease mortality rate in male and female flies exposed to paraquat, a Drosophila model for Parkinson's disease.

2.2 Cerium oxide nanoparticles protect Drosophila from paraquat-induced motor dysfunction. One of the hallmarks of PD is motor dysfunction, induced by loss of dopaminergic neurotransmission. Paraquat exposure in Drosophila also induces dopaminergic neuronal loss. Meulener (2005); and Cicchetti (2005). Using the Drosophila model detailed above, we assessed the effects of CeONP on motor dysfunction in response to paraquat challenge. Motor function was assessed in *drosophila* by examining a) total vertical activity and b) ability to ascend the vial to an 8 cm height, using a Trikinetics activity monitor.

For measurement of total vertical activity, an empty vial containing 10 flies was placed vertically in the monitor, which has 3 levels at which upward movement of flies can be measured, 3, 6 and 8 cm. Movement of a fly past a given level is registered as the fly crosses a beam of light. For a vial of 10 flies, the monitor assesses the number of times a fly crosses the light path at each respective height in the vial. The total number of beam crosses at all heights is then divided by the number of flies in the measurement group, giving a measure of activity/fly. Activity was monitored for 15 minutes per vial, for all flies within the group. All activity measurements were made at least 2 hrs after first exposure to light for the day, and 2 hrs prior to the lights turning off, to assure that measurement was not affected by diurnal activity changes.

Figure 11A:
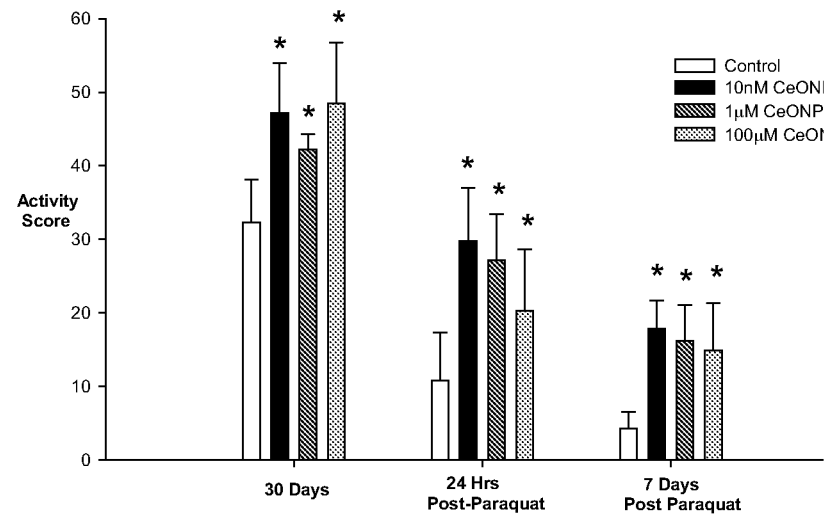
FIGS. 11A and 11B are bar graphs that show that cerium oxide nanoparticles preserve motor function in paraquat-challenged female and male Drosophila.
Figure 11B:
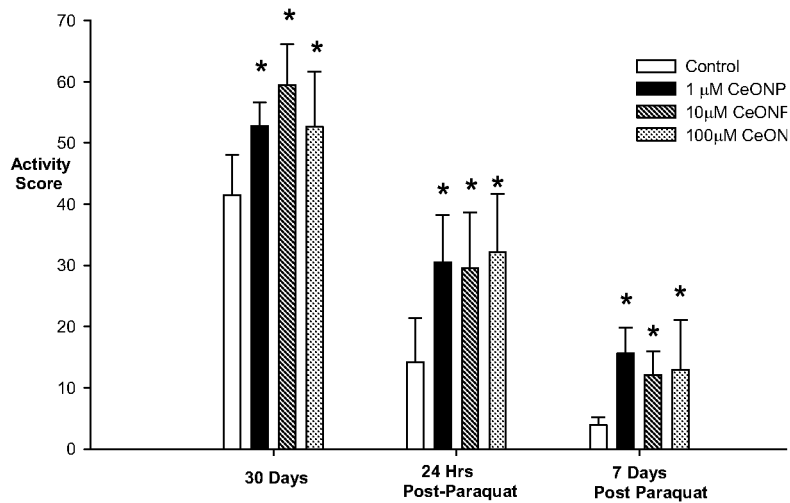

The effect of CeONP on total activity of paraquat-treated female flies is shown in FIG. 11A. Activity was first measured just prior to paraquat exposure (at 30 days of age) (first set of bars). As shown in FIG. 11A, middle aged CeONP fed flies had higher levels of activity than middle aged control flies, consistent with previous work demonstrating that CeONP preserve motor function in aging flies. Twenty-four hours (24 hrs) post paraquat (second group of bars), flies treated with paraquat alone exhibited a substantial decline in total activity. However the decline in activity post-paraquat was significantly less in CeONP fed flies. The effects persisted through 7 days post paraquat (last group of bars). Similar results were observed in male Drosophila, shown in FIG. 11B. These results demonstrate that CeONP preserves motor function in paraquat-treated flies.

Figure 12A:
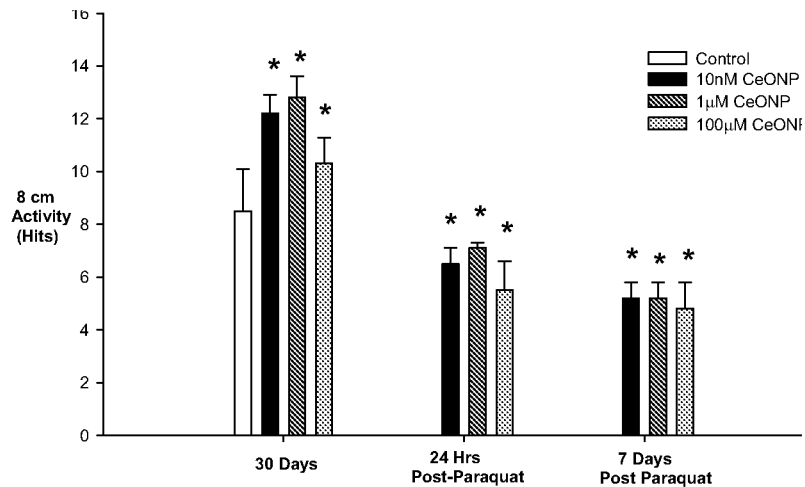
FIGS. 12A and 12B are bar graphs that show that cerium oxide nanoparticles preserve the climbing motor function of paraquat-challenged female and male Drosophila.
Figure 12B:
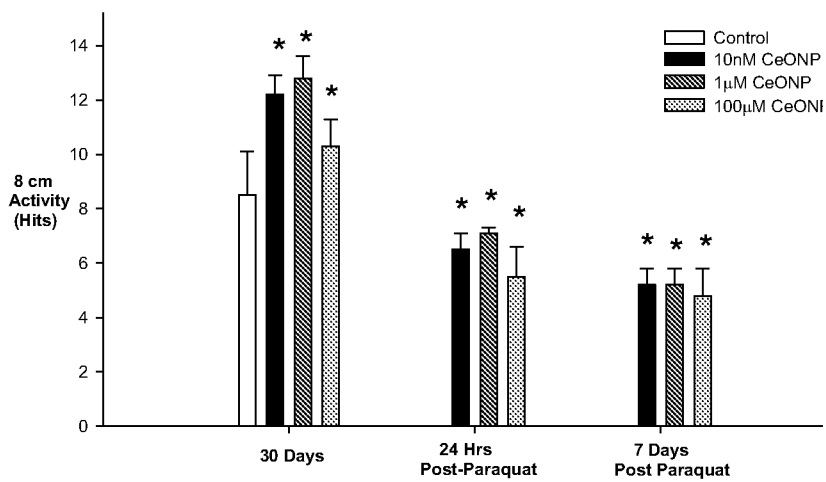

In addition to measuring total activity, we also measured the number of times flies ascended the vial to the 8 cm height, a measurement of the robustness of motor activity. FIG. 12A shows the ability of female flies to ascend to 8 cm at 30 days of age, prior to paraquat exposure. Once again, CeONP treated females showed enhanced ability to ascend to the 8 cm height, as compared to controls. Twenty-four hours (24 hrs) post paraquat, control flies were unable to ascend to 8 cm. This decline in function persisted through 7 days post-paraquat in all surviving flies. However surviving CeONP treated flies retained some ability to ascend to this level, which persisted in flies surviving 7 days post paraquat. Similar results were observed for male flies (FIG. 12B), where CeONP treated males were able to climb to 8 cm more often than controls. In particular, after treatment with 10 mM paraquat, controls were unable to climb the walls of the vial to this height, while CeONP preserved this motor function in surviving flies.

Taken together, these activity measurements demonstrate that CeONP reduces motor dysfunction in a Drosophila model of PD.

III. Mitochondrial Diseases and Mitochondrial Dysfunction.

Figure 13:
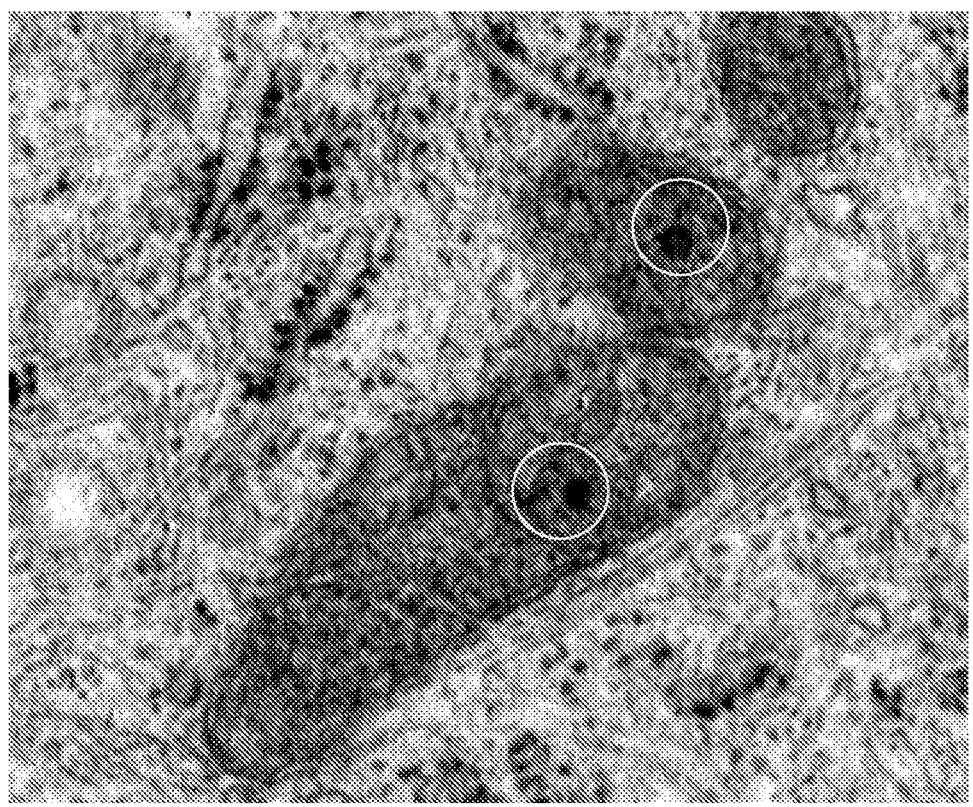
FIG. 13 is an electron micrograph that shows CeONP localized in mitochondria of mixed organotypic neuronal cultures.

3.1. Cerium oxide nanoparticles localize, in part, to mitochondria. Previous work has shown that CeONP readily enter cells and tissues and localize to cytoplasmic areas. See, e.g., WO 2007/002662; Rzigalinski (2006); Rzigalinski I (2006); Rzigalinski II (2006); Rzigalinski 2005; and Singh 2007. However, CeONP also localize, in part, to mitochondria, as shown in FIG. 13. Their role within the mitochondria has not been identified. To assess the effects of CeONP on cell demise associated with mitochondrial dysfunction, we utilized rotenone. Rotenone inhibits mitochondrial energy production through inhibition of Complex 1, and disrupts oxidative phosphorylation and the flow of electrons through the electron transport chain. This decreases ATP production and disrupts mitochondrial membrane potential (MMP).

3.2. Cerium oxide nanoparticles protect cells from death associated with inhibition of mitochondrial Complex I with rotenone. We exposed mixed organotypic rat brain cell cultures to CeONP (10 nM) or saline on day 10 in vitro, for 48 hrs. On day 14 in vitro, cultures were exposed to the mitochondrial Complex I inhibitor, rotenone (1 μM), for 24 hrs, and cell death was determined by propidium iodide uptake according to a published methodology. See, e.g., Ahmed (2002); and Ahmed, S. M., Rzigalinski, B. A., Willoughby, K. A., Sitterding, H. A., & Ellis, E. F (2000), Stretch-induced injury alters mitochondrial membrane potential and cellular ATP in cultured astrocytes and neurons, J. Neurochem., 74, 1951-1960, the disclosures of which are hereby incorporated by reference in their entirety.

Figure 14:
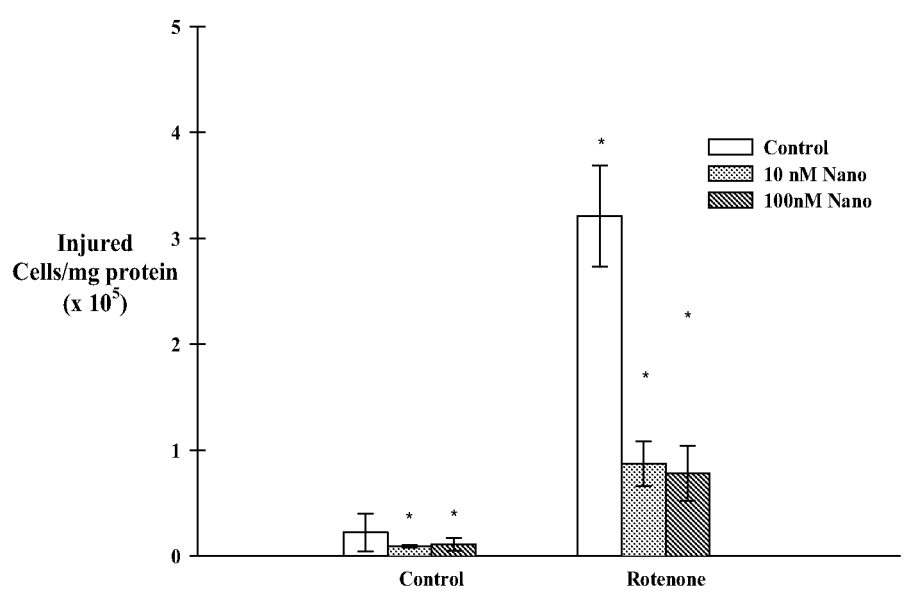
FIG. 14 is a bar graph that shows that cerium oxide nanoparticles protect mixed organotypic brain cell cultures from cell injury induced by rotenone.

CeONP treatment significantly reduced cell injury induced by rotenone. As shown in FIG. 14, CeONP significantly reduced propidium iodide uptake after rotenone exposure, suggesting that CeONP protects cells from damage associated with inhibition of mitochondrial Complex I. The organotypic cultures examined contained an astrocyte monolayer growing on the bottom of the culture well, with a layer of neurons attached to the top of the astrocytes. Although propidium iodide uptake does not differentiate between astrocytes and neurons, it appeared that the primary cell type taking up propidium iodide at 24 hrs post-rotenone were neurons, due to the increased propidium iodide staining observed in the cells above the confluent astrocyte monolayer. In CeONP-treated cultures, this neuronal layer appeared to be largely viable, without propidium iodide uptake.

3.3. Cerium oxide nanoparticles protect cells from mitochondrial failure associated with inhibition of mitochondrial complex I with rotenone. We also examined mitochondrial membrane potential (MMP) in rotenone-treated cells. MMP is a measurement of the ability of mitochondrial to undergo oxidative phosphorylation and produce ATP for cellular energy. MMP is decreased in dysfunctional mitochondria and in mitochondrial associated with several diseases including PD, AD, and mitochondrial disorders.

For these experiments, cells were treated with CeONP or saline for 48 hrs as described above, followed by rotenone (1 μM). MMP was measured 6 hrs post rotenone using Rhodamine 123 (Rh123) as previously described. Ahmed (2002); and Ahmed (2000), the disclosures of which are hereby incorporated by reference in their entirety.

Figure 15:
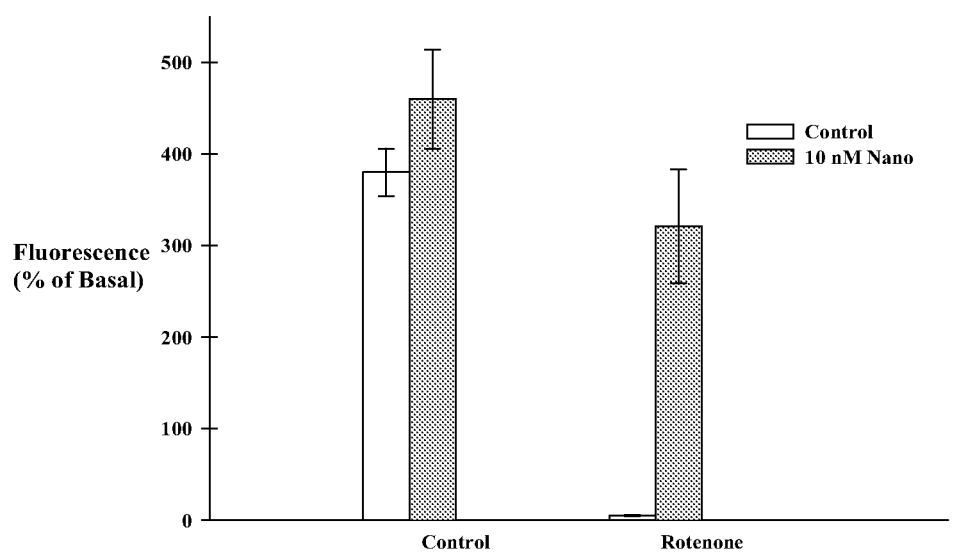
FIG. 15 is a bar graph that shows that cerium oxide nanoparticles preserve mitochondrial membrane potential after rotenone challenge.

As shown in FIG. 15, MMP was slightly higher in CeONP treated controls as compared to untreated controls treated (first 2 bars), however this was not significant. At 6 hrs post-rotenone, MMP declined dramatically in rotenone challenged cells, and rotenone almost completely abolished MMP in untreated controls. However MMP was preserved in CeONP-treated cells challenged with rotenone. Taken together, these results suggest that CeONP protects cells from damage to Complex I of the electron transport chain and preserves mitochondrial function. Thus, CeONP can be used as an effective treatment of mitochondrial diseases and diseases associated with mitochondrial damage. CeONP can also be effective in treating conditions involving toxic exposures to compounds that induce mitochondrial dysfunction, such as rotenone, cyanide, carbon monoxide, polychlorinated biphenyls (PCBs) and other mitochondrial toxins.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

The invention claimed is:

1. A method of treating a subject for Alzheimer's Disease, Huntington's Disease, Parkinson's Disease, or amyotrophic lateral sclerosis (ALS), said method comprising:
   administering a non-agglomerating composition comprising cerium oxide nanoparticles having an average particle diameter size of about 10 nm to about 20 nm in an amount sufficient to provide a therapeutically effective dose of about 10 ng, 50 ng, 100 ng, 500 ng, 1 µg, 5 µg, 10 µg, or 50 µg per kg body mass to a subject having Alzheimer's Disease, Huntington's Disease, Parkinson's Disease, or amyotrophic lateral sclerosis (ALS).

2. The method according to claim 1, wherein the non-agglomerating composition includes a carrier without any phosphate buffer.

3. A method of treating a subject for a mitochondrial disease or suffering from the effects of a mitochondrial toxin, comprising:
   administering a non-agglomerating composition comprising cerium oxide nanoparticles having an average particle diameter size of about 10 nm to about 20 nm in an amount sufficient to provide a therapeutically effective dose of about 10 ng, 50 ng, 100 ng, 500 ng, 1 µg, 5 µg, 10 µg, or 50 µg per kg body mass to a subject having mitochondrial disease or suffering from the effects of a mitochondrial toxin.

4. The method according to claim 3, wherein the effects of mitochondrial toxins result from exposure of a cell to rotenone, cyanide, carbon monoxide, or polychlorinated biphenyls (PCBs).

5. The method according to claim 4, wherein the effects of mitochondrial toxins are mitochondrial failure from inhibition of electron transport in the mitochondria.

6. The method of claim 3, wherein the subject has a mitochondrial disease.

* * * * *